United States Patent [19]

Böger et al.

[11] 4,234,573
[45] Nov. 18, 1980

[54] 1-TRIMETHYLSILYLPHENYL-3-MONO- AND -DI-HALOBENZOYL-UREAS, INSECTICIDAL COMPOSITIONS CONTAINING THEM AND THEIR USE IN CONTROLLING INSECT PESTS

[75] Inventors: Manfred Böger, Weil am Rhein, Fed. Rep. of Germany; Jozef Drabek, Oberwil, Switzerland

[73] Assignee: Ciba-Geigy Corporation, Ardsley, N.Y.

[21] Appl. No.: 46,288

[22] Filed: Jun. 7, 1979

[30] Foreign Application Priority Data

Jun. 15, 1978 [CH] Switzerland .................. 6533/78

[51] Int. Cl.³ .................. A01N 55/00; C07F 7/02
[52] U.S. Cl. .................. 424/184; 556/421
[58] Field of Search .................. 424/184; 260/448.2 B

[56] References Cited

FOREIGN PATENT DOCUMENTS 1324293  7/1973  United Kingdom .................. 424/322

Primary Examiner—Douglas W. Robinson
Attorney, Agent, or Firm—John J. Maitner

[57] ABSTRACT

Compounds of the formula I

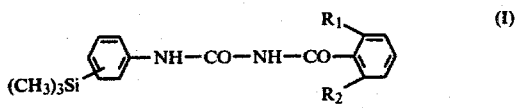

wherein $R_1$ is fluorine or chlorine and $R_2$ is hydrogen, fluorine or chlorine having valuable insecticidal properties.

8 Claims, No Drawings

1-TRIMETHYLSILYLPHENYL-3-MONO- AND -DI-HALOBENZOYL-UREAS, INSECTICIDAL COMPOSITIONS CONTAINING THEM AND THEIR USE IN CONTROLLING INSECT PESTS

The present invention relates to novel 1-trimethylsilylphenyl-3-mono- and di-halobenzoyl-ureas which are effective against insect pests, to processes for producing these ureas, and to insecticidal compositions containing them as active ingredients, and to processes for controlling insect pests by use of the novel compounds.

1-Phenyl-3-benzoyl-ureas having a pesticidal action, particularly an insecticidal action, are known (see G.B. Patent Specification No. 1,324,293). According to the present invention, novel compounds of this type which have a particularly intensive action against insect pests are provided.

The novel 1-trimethylsilylphenyl-3-mono- and -di-halobenzoyl-ureas according to the present invention correspond to the formula I

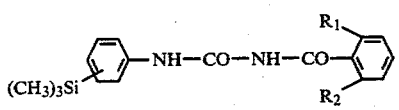

wherein $R_1$ is a fluorine or chlorine atom, and $R_2$ is a hydrogen, fluorine or chlorine atom.

Compounds preferred on account of their action are the compounds of the formula IA

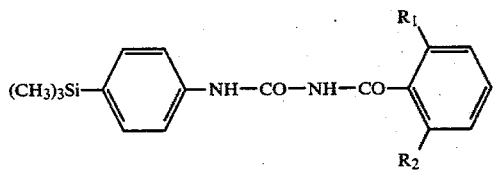

wherein $R_1$ and $R_2$ have the meanings already defined under the formula I.

The compounds of the formula I according to the invention are advantageously obtained, using methods known per se, by reacting for example (a) a compound of the formula II

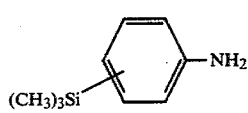

with a compound of the formula III

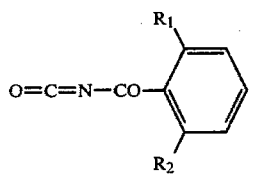

or (b) a compound of the formula IV

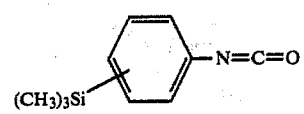

with a compound of the formula V

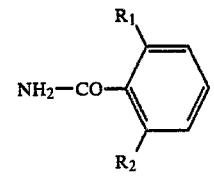

where in the formulae III and V the symbols $R_1$ and $R_2$ have the meanings already defined under the formula I.

Preferably, the process (a) is performed at a reaction temperature of between 20° and 40° C., optionally in the presence of a catalytic amount of a base (for example tertiary amines, pyridine and "Dabco"), and the process (b) at a reaction temperature of between 100° and 150° C. Both processes can be performed at normal or slightly elevated pressure, preferably in the presence of solvents or diluents which are inert to the reactants.

Suitable solvents or diluents are for example: ethers and ethereal compounds such as diethyl ether, di-isopropyl ether, dioxane and tetrahydrofuran; aliphatic and aromatic hydrocarbons, especially benzene, toluene and xylenes; and ketones such as acetone, methyl ethyl ketone and cyclohexanone.

The starting materials of the formulae II, III, IV and V are known, or they can be produced by methods analogous to known methods.

The compounds of the formula I, and particularly those of the formula IA, according to the invention, are distinguished by an intense insecticidal action, with their action against all stages of development (adults, pupae, larvae and also eggs) of insects of the order Lepidoptera and particularly of the family Noctuidae (for example Spodoptera littoralis and Laspeyresia pomonella) being especially pronounced. Accordingly, the compounds of the formula I and IA are particularly suitable according to the invention for controlling insects which damage plants, in crops of useful plants and ornamental plants, especially in cotton, fruit and vegetable crops.

The insecticidal action of the compounds according to the invention can be substantially broadened and adapted to suit given circumstances by the addition of other insecticides and/or acaricides. Suitable additives are for example: organic phosphorus compounds; nitrophenols and derivatives thereof; formamidines; ureas; pyrethrin-like compounds; carbamates and chlorinated hydrocarbons.

The compounds of the formula I can be used on their own or together with suitable carriers and/or additives. Suitable additives can be solid or liquid and they correspond to the substances common in formulation practice, such as natural or regenerated substances, solvents, dispersing agents, wetting agents, adhesives, thickeners, binders and/or fertilisers.

For application, the compounds of the formula I can be processed into the form of dusts, emulsion concentrates, granulates, dispersions, sprays, solutions or suspensions, using customary methods of formulation which form part of the common knowledge related to application techniques.

The compositions according to the invention are produced in a manner known per se by the intimate mixing and/or grinding of the active substances of the formula I with suitable carriers, optionally with the addition of dispersing agents or solvents which are inert to the active substances. The active substances (compounds of the formula I) can be obtained and used in the following forms:

Solid Preparations dusts, scattering agents, granules (coated granules, impregnated granules and homogeneous granules);

Liquid Preparations (a) water-dispersible wettable powders, pastes and emulsions;
(b) solutions.

The content of active substance (compound of the formula I) in the compositions described above is between 0.1 and 95%; it is to be mentioned in this connection that with application from an aeroplane or from other suitable application devices, also higher concentrations may be used.

The active substances of the formula I can be formulated for example as follows:

Dusts

The following substances are used to produce (a) a 5% dust and (b) a 2% dust:

(a)

5 parts of active substance, and
95 parts of talcum;

(b)

2 parts of active substance,
1 part of highly dispersed silicic acid, and
97 parts of talcum.

The active substance is mixed and ground with the carriers.

Granulate

The following ingredients are used to produce a 5% granulate:
5 parts of active substance,
0.25 part of epichlorohydrin,
0.25 part of cetyl polyglycol ether,
3.50 parts of polyethylene glycol, and
91 parts of kaolin (particle size 0.3-0.8 mm).

The active substance is mixed with epichlorohydrin and dissolved in 6 parts of acetone; the polyethylene glycol and cetyl polyglycol ether are then added. The solution thus obtained is sprayed onto kaolin, and the acetone is subsequently evaporated off in vacuo.

Wettable powders

The following constituents are used to produce (a) a 40% wettable powder, (b) and (c) a 25% wettable powder and (d) a 10% wettable powder:

(a)

40 parts of active substance,
5 parts of sodium lignin sulfonate,
1 part of sodium dibutyl-naphthalene sulfonate, and
54 parts of silicic acid;

(b)

25 parts of active substance,
4.5 parts of calcium lignin sulfonate,
1.9 parts of Champagne chalk/hydroxyethyl cellulose mixture (1:1),
1.5 parts of sodium dibutyl-naphthalene sulfonate,
19.5 parts of silicic acid,
19.5 parts of Champagne chalk, and
28.1 parts of kaolin;

(c)

25 parts of active substance,
2.5 parts of isooctylphenoxy-polyoxyethylene-ethanol,
1.7 parts of Champagne chalk/hydroxyethyl cellulose mixture (1:1),
8.3 parts of sodium aluminium silicate,
16.5 parts of kieselguhr, and
46 parts of kaolin; and (d)

10 parts of active substance,
3 parts of a mixture of the sodium salts of saturated fatty alcohol sulfates,
5 parts of naphthalenesulfonic acid/formaldehyde condensate, and
82 parts of kaolin.

The active substance is intimately mixed in suitable mixers with the additives, and the mixture is then ground in the appropriate mills and rollers to obtain wettable powders which can be diluted with water to give suspensions of the concentration desired.

Emulsifiable concentrates

The following substances are used to produce (a) a 10% emulsifiable concentrate, (b) a 25% emulsifiable concentrate and (c) a 50% emulsifiable concentrate:

(a)

10 parts of active substance,
3.4 parts of epoxidised vegetable oil,
3.4 parts of a combination emulsifier consisting of fatty alcohol polyglycol ether and alkylarylsulfonate calcium salt,
40 parts of dimethylformamide, and
43.2 parts of xylene;

(b)

25 parts of active substance,
2.5 parts of epoxidised vegetable oil,
10 parts of alkylarylsulfonate/fatty alcohol polyglycol ether mixture,
5 parts of dimethylformamide, and
57.5 parts of xylene; and (c)

50 parts of active substance,
4.2 parts of tributylphenol-polyglycol ether,
5.8 parts of calcium-dodecylbenzenesulfonate,
20 parts of cyclohexanone, and
20 parts of xylene.

Emulsions of the required concentration can be prepared from these concentrates by dilution with water.

Spray

The following constituents are used to produce (a) a 5% spray:
5 parts of active substance,
1 part of epichlorohydrin, and
94 parts of ligroin (boiling limites 160°–190° C.).

The Examples which follow serve to further illustrate the invention.

EXAMPLE 1

Production of 1-(4-trimethylsilylphenyl)-3-(2,6-difluorobenzoyl)-urea

A solution of 6.0 g of 2,6-difluorobenzoylisocyanate in 20 ml of toluene was added dropwise at room temperature to a mixture of 5.4 g of 4-trimethylsilylaniline, 50 ml of toluene and 100 mg of Dabco ®. The reaction mixture obtained was subsequently stirred at 60° C. for 3 hours. The reaction mixture was concentrated by evaporation, and the residue was recrystallised from acetone to obtain 1-(4-trimethylsilylphenyl)-3-(2,6-difluorobenzoyl)-urea of the formula

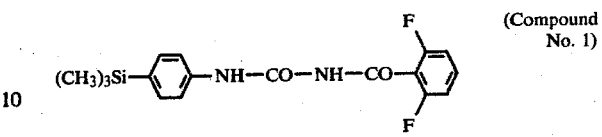

(Compound No. 1)

as a white powder having a melting point of 187°–189° C.

The following compounds can be produced in an analogous manner:

| Compound No. | Structure | m.p. |
|---|---|---|
| 2. | (CH₃)₃Si—⌬—NH—CO—NH—CO—⌬(2-F) | m.p. 136–138° C. |
| 3. | (CH₃)₃Si—⌬—NH—CO—NH—CO—⌬(2-F, 6-Cl) | |
| 4. | (CH₃)₃Si—⌬—NH—CO—NH—CO—⌬(2,6-Cl₂) | m.p. 178–179° C. |
| 5. | (CH₃)₃Si—⌬—NH—CO—NH—CO—⌬(2-Cl) | m.p. 157–158° C. |
| 6. | 3-(CH₃)₃Si—⌬—NH—CO—NH—CO—⌬(2,6-F₂) | m.p. 175–176° C. |
| 7. | 3-(CH₃)₃Si—⌬—NH—CO—NH—CO—⌬(2-F) | m.p. 136–138° C. |
| 8. | 3-(CH₃)₃Si—⌬—NH—CO—NH—CO—⌬(2-F, 6-Cl) | |

| Compound No. | | |
|---|---|---|
| 9. | ![structure] Ar(CH3)3Si-NH-CO-NH-CO-Ar(Cl,Cl) | m.p. 179–180° C. |
| 10. | ![structure] Ar(CH3)3Si-NH-CO-NH-CO-Ar(Cl) | m.p. 150–152° C. |
| 11. | ![structure] Ar((CH3)3Si)-NH-CO-NH-CO-Ar(F,F) | |

EXAMPLE 2

Insecticidal stomach poison action: *Spodoptera littoralis*, *Heliothis virescens* and *Dysdercus fasciatus*

Cotton plants were sprayed with an aqueous emulsion containing 0.05% of the compound to be tested (obtained from a 10% emulsifiable concentrate). After drying of the coating, larvae of the species
(a) Spodoptera littoralis (L3),
(b) Heliothis virescens (L3/L4), or
(c) Dysdercus fasciatus (L5)
were settled on each of the plants. Two plants were used per test compound and per test species, and an assessment of the destruction of larvae was made 2, 4, 24 and 48 hours after commencement of the test.

The test was carried out at 24° C. with 60% relative humidity.

Compounds according to Example 1, particularly the compounds 1 to 5, exhibited in the above test a favourable stomach poison action against larvae of the species mentioned.

EXAMPLE 3

Action against eggs of the species *Spodoptera littoralis* and *Laspeyresia pomonella*

One-day old eggs of the species *Spodoptera littoralis* and *Laspeyresia pomonella* were deposited onto an aluminium foil, and then immersed for 1 minute in an emulsion containing 40% of the compound to be tested. After drying, the eggs of both species were kept at a temperature of 28° C. with 50% relative humidity. An assessment of the number of unhatched eggs was made in the case of the species Spodoptera littoralis 4 days after treatment with the test emulsion, and in the case of the species Laspeyresia pomonella 6 days after treatment with the test emulsion.

Compounds according to Example 1, especially the compounds 1 to 5, exhibited in the above test an intensive action against eggs of the two test species mentioned (number of hatched eggs negligible to 0%).

What is claimed is:

1. A compound of the formula I

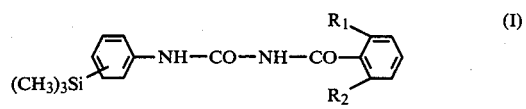

wherein $R_1$ is fluorine or chlorine and $R_2$ is hydrogen, fluorine or chlorine.

2. A compound as claimed in claim 1 of the formula IA

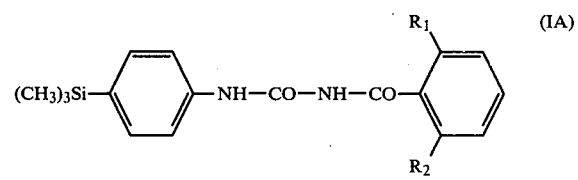

3. A compound as claimed in claim 2 of the formula

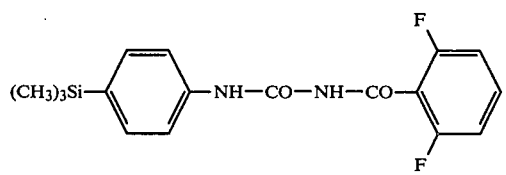

4. A compound as claimed in claim 2 of the formula

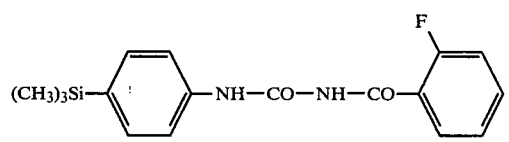

5. A compound as claimed in claim 2 of the formula

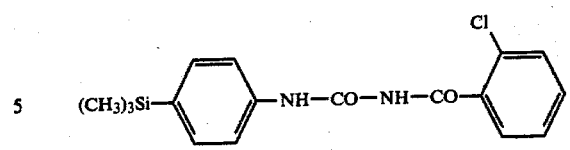

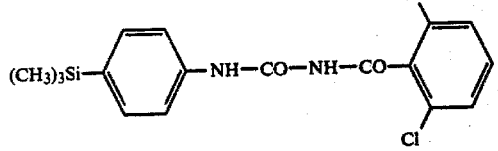

6. A compound as claimed in claim 2 of the formula

7. An insecticidal composition comprising an insecticidally effective amount of a compound as claimed in any one of claims 1, 2 or 3 together with an inert, solid or liquid pesticide diluent or carrier therefor.

8. A method of controlling insect pests, which comprises applying to said insects or the locus thereof an insecticidally effective amount of a compound as claimed in any one of claims 1, 2 or 3.